United States Patent
Csernica et al.

(10) Patent No.: US 6,387,356 B1
(45) Date of Patent: May 14, 2002

(54) COSMETIC COMPOSITION

(75) Inventors: Jeffrey Joseph Csernica, Lewisburg, PA (US); Peter R. Hilliard, Jr., Far Hills; Paul Joseph Vincenti, Jefferson, both of NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 09/492,603

(22) Filed: Jan. 27, 2000

(51) Int. Cl.$^7$ ................................................. A61K 7/32
(52) U.S. Cl. ........................................ 424/65; 424/401
(58) Field of Search ............................. 424/401, 59, 65

(56) References Cited

U.S. PATENT DOCUMENTS

| | | | |
|---|---|---|---|
| 3,824,085 A | * 7/1974 | Teng et al. .................. 44/7 |
| 4,383,988 A | * 5/1983 | Teng et al. .................. 424/68 |
| 4,508,705 A | 4/1985 | Chaudhuri et al. .......... 424/47 |
| 4,803,195 A | 2/1989 | Holzner ....................... 512/4 |
| 4,963,591 A | 10/1990 | Fourman et al. ........... 514/944 |
| 5,025,004 A | 6/1991 | Wu et al. .................... 514/165 |
| 5,869,600 A | 2/1999 | Causton et al. ............. 528/422 |
| 5,948,430 A | 9/1999 | Zerbe et al. ................ 424/435 |
| 5,989,570 A | 11/1999 | Lion et al. .................. 424/401 |

FOREIGN PATENT DOCUMENTS

EP  WO 95/27473  4/1994

* cited by examiner

*Primary Examiner*—Jose' G. Dees
*Assistant Examiner*—Konata M. George
(74) *Attorney, Agent, or Firm*—Rosemary M. Miano

(57) ABSTRACT

Personal care products are disclosed which comprises an alcohol based composition which includes a film forming system comprising cellulose esters, which product (1) is capable of forming a thin film on the skin which film is characterized by selected hardness, and water transport properties and (2) reduces or eliminates wetness such as wetness caused by perspiration. These compositions can be used in cosmetic products, especially antiperspirants, deodorants, and combination antiperspirant/deodorants. The compositions comprise: (a) an alcohol based solvent system; and (b) a cellulose ester component which is soluble in alcohol.

10 Claims, 1 Drawing Sheet

COSMETIC COMPOSITION

BACKGROUND OF THE INVENTION

This invention relates to an alcohol based cosmetic composition which includes a film-forming system comprising cellulosic derivatives capable of forming thin films on the skin and which films are characterized by selected hardness, solution viscosity, and water transport properties. The compositions of this invention are useful in reducing or eliminating wetness such as wetness caused by perspiration. These compositions can be used in cosmetic products where such an effect is desirable, for example, in underarm products such as antiperspirants and in makeup bases.

There continues to be ongoing efforts to discover improved cosmetic compositions which are able to reduce or eliminate wetness. These efforts have included the development of film-forming compositions such as are described in U.S. Pat. No. 4,803,195 to Holzner. This patent describes personal care compositions comprising aqueous emulsions which contain a perfume base and a solid film-forming substrate such as carboxymethyl cellulose, methyl cellulose and hydroxymethyl cellulose. These compounds are generally classified as gums. The compositions of this patent require the addition of an antiperspirant active to achieve an antiperspirant effect.

U.S. Pat. No. 4,963,591 to Fourman et al describes skin care cosmetic formulations which include a cellulosic polymer/solvent system, especially containing cellulosic ethers, capable of dispersing thin, substantive films on skin. These compositions are characterized by strong adherence to the skin and high resistance to removal by water. These properties make such compositions particularly useful for sunscreen compositions.

U.S. Pat. No. 4,508,705 to Chaudhuri et al discloses antiperspirant compositions comprising a moisture-absorbent water insoluble polymer which is substantially dry to the touch when swollen with water, a surfactant having a melting point from 30–75 degrees C., and an organic solvent in which the polymer is substantially insoluble. Preferred polymers are derived from anionic polyelectrolytes. Sodium and ammonium cross-linked starches are described as being particularly preferred as absorbent materials.

U.S. Pat. No. 5,025,004 to Wu et al teaches a process for preparing water dispersible polymeric compositions which are suitable for coating medicaments or for use in cosmetic formulations and formulations made therefrom. The invention includes the use of a water-in-oil emulsifier and an oil-in-water emulsifier which is water insoluble. Examples of water insoluble polymers include cellulose acetate butyrate and cellulose acetate propionate.

U.S. Pat. No. 5,508,024 to Tranner discloses an antiperspirant composition consisting essentially of an effective amount of a non-toxic water-insoluble occlusive film-forming polymer which can be applied to the skin to reduce perspiration. The types of water-insoluble polymers described in this reference include alkyl olefinic acid amide/olefinic acid or ester copolymer, for example, octylacryl amide or propenamide/acrylates-copolymer, alone or in combination with a PVP-linear alpha-olefin copolymer. Optionally, active antiperspirant ingredients can be added to the compositions.

PCT application WO 95/27473 assigned to Gillette teaches novel film-forming polymers with antiperspirant properties wherein the polymers have a carbon backbone and pendant groups which contain quaternized nitrogen atoms (at least one substituent on the quaternized nitrogen being hydrophobic) and which contain at least 8 carbon atoms. For use as antiperspirants, they are dissolved or suspended in a non-aqueous carrier with a small amount of water.

While each of the references described above have their own particular utility and chemistry, none of these references describe the subject of the present invention. Specifically there still remains a need for new and useful topical compositions which can be applied to the skin and which are capable of reducing or eliminating wetness such as wetness due to perspiration. More particularly, there remains a desire for formulations using cellulosic polymers that are non-water absorbing and which are capable of reducing or eliminating wetness such as wetness due to perspiration.

It is a further object of the invention to provide compositions which are suitable for reducing or eliminating wetness when applied to the skin, which form films with desirable mildness and aesthetics.

It is yet another object of the present invention to provide compositions which are suitable for reducing or eliminating wetness when applied to the skin and which do not require the presence of an antiperspirant active to achieve an antiperspirant effect.

It is an additional object of the present invention to provide compositions which are suitable for reducing or eliminating wetness when applied to the skin and which can be used as a make-up base.

Another object of the invention includes providing compositions which are suitable for reducing or eliminating wetness when applied to the skin and which can be formed into a variety of physical forms such as sticks, gels and liquids for cosmetic uses. These and other objects will be apparent from the following description of the invention.

SUMMARY OF THE INVENTION

This invention comprises a personal care product which comprises an alcohol based composition which includes a film forming system comprising cellulose esters, which product (1) is capable of forming a thin film on the skin which film is characterized by selected hardness, and water transport properties and (2) reduces or eliminates wetness such as wetness caused by perspiration. These compositions can be used in cosmetic products where such an effect is desirable, for example, in underarm products such as antiperspirants, deodorants, combination antiperspirant/deodorants and in makeup bases. The compositions comprise: (a) an alcohol based solvent system; and (b) a cellulose ester which is soluble in alcohol.

DETAILED DESCRIPTION OF THE INVENTION

Figure 1:
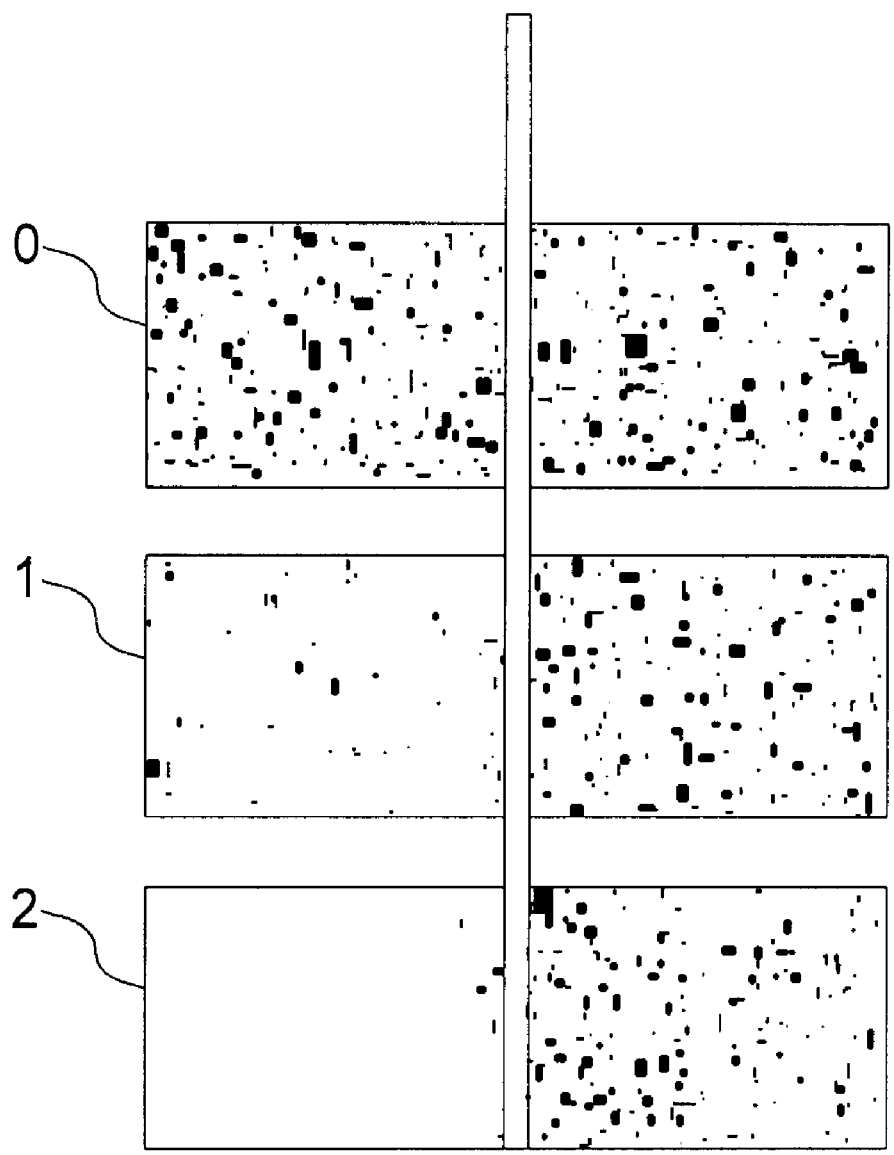
FIG. 1 shows a representative sample of the extent over which sweat covered a selected forearm area in the Forearm Sweat Reduction Test described below. The number scale on the left labeled as Efficacy Rank may be used as the scale against which other tests are rated. The rectangles to the right of the black line are representative of the amount of coverage obtained when no film was applied and the rectangles to the left of the black line are representative of various amounts of coverage obtained for the numerical ranking associated with the number next to the rectangle. Thus, a "0" ranking looks about the same as the control, a "1" ranking has a less dense dot pattern and a "2" ranking has very few dots, wherein the dots are representative of the degree of coverage caused by sweat droplets.

The cosmetic compositions of this invention comprise:

(a) an alcohol-based solvent system selected from the group consisting of
  (i) a volatile aliphatic alcohol containing up to 10 weight percent water and having a solubility parameter in the range of 20.5–31.0 $(MPa)^{1/2}$, wherein the alcohol is selected from the group consisting of ethanol, n-propanol, isopropanol, n-butanol, isobutanol and mixtures of any of the foregoing; and
  (ii) a solvent as described in part (i) in combination with a nonvolatile polyhydric glycol selected from the group consisting of propylene glycol, dipropylene glycol, tripropylene glycol, other polypropylene glycols (for example, PPG-425 from Dow Chemical, Midland, Mich.) and glycerol, (specific examples of suitable solvents include ethanol from group (i) and propylene glycol from group (ii)); provided that the ratio of propylene glycol dipropylene glycol, tripropylene glycol, other polypropylene glycols to aliphatic alcohol does not exceed 1:5; and
(b) a cellulose ester (or a mixture of cellulose esters) which is:
  (i) soluble in the alcohol-based solvent system (for example, 100 % alcohol or an alcohol/water mixture having up to 10% water) in an amount of 0.5–20% (and particularly 5–10%) by weight solution of cellulose ester with the alcohol based solvent system based on the total composition; and
  (ii) has an ester group formed with 2–6 carbons and an average OH content of at least 3.00%.

Note that in one embodiment of the invention, the solvent system is not solely comprised of a polyhydric alcohol, for example, the solvent system can be a propylene glycol/ethanol system. In particular, at polymer/solvent ratios of 1:10 the ratio of polyhydric to monohydric alcohols will typically not exceed 1:5 for cellulose esters.

The compositions of this invention are capable, when applied to skin, of forming a thin film (such as in the range of 0.1–10 microns) having a pencil hardness greater than or equal to 6B (see the scale in Table I), and absorbing at equilibrium less than 5 weight percent water when exposed to a condition of 75 percent relative humidity at 25 degrees C. In particular, it is desirable that the film forming system be made as a 5–10% solution with a viscosity of less than 5,000 centipoise, preferably less than 1,000 centipoise and most preferably less than 350 centipoise.

Optionally, the cosmetic compositions may also include one or more ingredients selected from the group consisting of emollients, surfactants, small particulates (for example, talc) plasticizers, fragrances, cosmetically active ingredients such as antiperspirant salts and antimicrobials, as well as one or more additional solidifying agents.

For purposes of the present invention the film-forming compositions comprise a cellulosic ester in an alcohol-based solvent delivery system. Mixtures of esters may also be used. The cellulosic esters can be selected from the group consisting of those having ester groups formed with from 2–6 carbons (including mixtures thereof) with an average hydroxyl content of greater than 3.00 weight percent.

Particular examples of cellulosic esters include cellulose acetate butyrate, and cellulose acetate propionate. It is important that the cellulosic esters be able to dissolve in the solvent system at the desired concentration in the range of 0.5–20 weight percent (particularly 5–10 percent) based on the total composition. For example, the polymers selected for the invention include those where the molecular weight and solubility characteristics of the polymer are such that they dissolve in ethanol or ethanol containing up to 10 weight percent water; such a polymer solution containing 10 weight percent polymer exhibits a viscosity of less than 5,000 centipoise ("cP"), particularly less than 1,000 cP, and especially less than 350 cP.

Particular polymers that provide clear solids in formulated products made in accordance with this invention include cellulose acetate butyrate (CAB 553-0.4, from Eastman Chemical Company, Kingsport, Tenn.); and cellulose acetate propionate (CAP 504-0.2 from Eastman). When prepared as 10 wt % solution in ethanol containing 10 wt % water, CAP 504-0.2 exhibits a solution viscosity of about 56 cP.

While it is not required for effectiveness that any antiperspirant active be present in the composition of this invention, it may be desirable to form compositions which contain at least some amount of an antiperspirant ingredient. One can select such ingredient from those known in the art including the group comprising aluminum chlorohydrate, aluminum chloride, aluminum sesquichlorohydrate, zirconyl hydroxychloride, and aluminum-zirconium glycine complexes. One or more of these antiperspirant actives can be added in an amount of from 10–25 weight % based on the overall composition, preferably 20–25 % to get a full antiperspirant effect. Particular materials include (but are not limited to) aluminum clilorohydroxide, aluminum chloride, aluminum sesquichlorohydroxide, zirconyl hydroxychloride, and aluminum chlorohydrol-propylene glycol complex. These include, by way of example (and not of a limiting nature), aluminum chlorohydrate, aluminum chloride, aluminum sesquichlorohydrate, zirconyl hydroxychloride, aluminum-zirconium glycine complex (for example, aluminum zirconium trichlorohydrex gly, aluminum zirconium pentachlorohydrex gly, aluminum zirconium tetrachlorohydrex gly and aluminum zirconium octochlorohydrex gly), aluminum chlorohydrex PG, aluminum chlorohydrex PEG, aluminum dichlorohydrex PG, and aluminum dichlorohydrex PEG. The aluminum-containing materials can be commonly referred to as antiperspirant active aluminum salts. Generally, the foregoing metal antiperspirant active materials are antiperspirant active metal salts. In the embodiments which are antiperspirant compositions according to the present invention, such compositions need not include aluminum-containing metal salts, and can include other antiperspirant active materials, including other antiperspirant active metal salts. Generally, Category I active antiperspirant ingredients listed in the Food and Drug Administration's Monograph on antiperspirant drugs for over-the-counter human use can be used. In addition, any new drug, not listed in the Monograph, such as aluminum nitratohydrate and its combination with zirconyl hydroxychlorides and nitrates, or aluminum-stannous chlorohydrates, can be incorporated as an antiperspirant active ingredient in antiperspirant compositions according to the present invention. Preferred antiperspirant actives that can be incorporated in the compositions of the present invention include the enhanced efficacy aluminum salts and the enhanced efficacy zirconium/aluminum salt-glycine materials, having enhanced efficacy due to improved molecular distribution, known in the art and discussed, for example, in PCT No. WO 92/19221 and EP 512 770 A1, the contents of which are incorporated by reference in their entirety herein.

The amount of antiperspirant active material incorporated in the stick composition of the present invention is, preferably, an antiperspirant effective amount; that is, an amount to reduce the flow of perspiration from the location (for example, axillary region of a human) to which the antiperspirant is applied. For deodorant products a level of from 0.5–20%, more particularly 0.5–5.0% by weight based on the entire weight of the composition is used. For an antiperspirant product an amount of 5.0–25%, particularly 5–20%, even more particularly 7–15%, and especially 7–12% by weight based on the total-weight of this composition may be used. The amount of antiperspirant material utilized is dependent on the efficacy of the specific antiperspirant material, as well as a maximum amount which avoids a reduction in clarity of the final product.

In one set of embodiments these antiperspirant active metal salts have a refractive index of at least 1.500, and include, but are not limited to, aluminum-zirconium tri-, tetra- and penta- chlorohydrate glycine complexes, which are coordination complexes of aluminum-zirconium tri-, tetra- or penta- chlorohydrate and glycine in which some of the water molecules normally coordinated to the metal have been displaced by the glycine. Illustrative antiperspirant active metal salts include aluminum-zirconium tetrachlorohydrex gly (for example, Reach AZP-908 and Reach 908-0, each manufactured by Reheis Inc., Berkeley Heights, N.J., which are coordination complexes of aluminum-zirconium tetrachlorohydrate and glycine in which some of the water molecules normally coordinated to the metal have been displaced by the glycine. The present invention is not limited to use of aluminum-zirconium tetrachlorohydrex gly, and other antiperspirant active metal salts (such as aluminum chlorohydrate), and/or other antiperspirant active materials, can be utilized in the stick composition of the present invention.

Particular examples of antiperspirant actives used in the underarm products of the invention include conventional aluminum and aluminum/zirconium salts, as well as aluminum/zirconium salts complexed with a neutral amino acid such as glycine, as known in the art. See each of European Patent Application Number. 512,770 A1 and PCT case WO 92/19221, the contents of each of which are incorporated herein by reference in their entirety, for disclosure of antiperspirant active materials. The antiperspirant active materials disclosed therein, including the acidic antiperspirant materials, can be incorporated in the compositions of the present invention if they are soluble in the active phase. Suitable materials include (but are not limited to) aluminum chlorides (various types including, for example, anhydrous form, hydrated form, etc.), zirconyl hydroxychlorides, zirconyl oxychlorides, basic aluminum chlorides, basic aluminum chlorides combined with zirconyl oxychlorides and hydroxychlorides, and organic complexes of each of basic aluminum chlorides with or without zirconyl oxychlorides and hydroxychlorides and mixtures of any of the foregoing. These include, by way of example (and not of a limiting nature), aluminum chlorohydrate, aluminum chloride, aluminum sesquichlorohydrate, aluminum chlorohydrol-propylene glycol complex, zirconyl hydroxychloride, aluminum-zirconium glycine complex (for example, aluminum zirconium trichlorohydrex gly, aluminum zirconium pentachlorohydrex gly, aluminum zirconium tetrachlorohydrex gly and aluminum zirconium octochlorohydrex gly), aluminum dichlorohydrate, aluminum chiorohydrex PG, aluminum chlorohydrex PEG, aluminum dichlorohydrex PG, aluminum dichlorohydrex PEG, aluminum zirconium trichlorohydrex gly propylene glycol complex, aluminum zirconium trichlorohydrex gly dipropylene glycol complex, aluminum zirconium tetrachlorohydrex gly propylene glycol complex, aluminum zirconium tetrachlorohydrex gly dipropylene glycol complex, and mixtures of any of the foregoing. The aluminum-containing materials can be commonly referred to as antiperspirant active aluminum salts. Generally, the foregoing metal antiperspirant active materials are antiperspirant active metal salts. In the embodiments which are antiperspirant compositions according to the present invention, such compositions need not include aluminum-containing metal salts, and can include other antiperspirant active materials, including other antiperspirant active metal salts. Generally, Category I active antiperspirant ingredients listed in the Food and Drug Administration's Monograph on antiperspirant drugs for over-the-counter human use can be used. In addition, any new drug, not listed in the Monograph, such as tin or titanium salts used alone or in combination with aluminum compounds (for example, aluminum-stannous chlorohydrates), aluminum nitratohydrate and its combination with zirconyl hydroxychlorides and nitrates, can be incorporated as an antiperspirant active ingredient in antiperspirant compositions according to the present invention. Preferred antiperspirant actives that can be incorporated in the compositions of the present invention include the enhanced efficacy aluminum salts and the enhanced efficacy aluminum/ zirconium salt-glycine materials, having enhanced efficacy due to improved molecular distribution, known in the art and discussed, for example, in PCT No. WO92/19221, the contents of which are incorporated by reference in their entirety herein.

Antiperspirant actives can be incorporated into compositions according to the present invention in amounts in the range of 0.1–30% (on an anhydrous solids basis), preferably 5–25%, by weight, of the total weight of the composition. The amount used will depend on the formulation of the composition. For example, at amounts in the lower end of the broader range (for example, 0.1–5%), the antiperspirant active material will not substantially reduce the flow of perspiration, but will reduce malodor, for example, by acting as a deodorant material.

Deodorant active materials can be selected from several types of materials:
(a) lesser amounts of antiperspirant actives, such as in the range of 0.1–5.0 percent by weight based on the total weight of the composition;
(b) fragrances, such as in the range of 0.5–3.0 percent by weight based on the total weight of the composition;
(c) effective amounts of antimicrobial agents, for example, 0.01–1.0 percent by weight based on the total weight of the composition; examples include bacteriostatic quaternary ammonium compounds (such as cetyl trimethyl-ammonium bromide, and cetyl pyridinium chloride), 2, 4, 4'-trichloro-2'-hydroxydiphenylether (Triclosan), N-(4-chlorophenyl)-N'-(3,4-dichlorophenyl)urea (Triclocarban), silver halides, octoxyglycerin (SENSIVA™ SC 50) and various zinc salts (for example, zinc ricinoleate). Triclosan or Triclocarban can, illustratively, be included in an amount of from 0.05% to about 0.5% by weight, of the total weight of the composition.

It is also possible to match the refractive index of the components in the compositions so as to reduce or eliminate the residue left after application.

With regard to fragrances, it has been found that the retention of fragrance is enhanced by the compositions of this invention. Dissolving a fragrance component into the polymer solution, such as d-limonene allows for a greater substantivity of the fragrance material, thereby maintaining a longer deodorancy effect and/or hedonic benefit to the user. This feature is helpful in deodorant and antiperspirant products.

Plasticizers may be added to enhance the film forming properties of the composition and contribute to the reduction of visible residue. While it has been observed that some cracking of the film formed with several compositions of this invention does not appear to affect the performance of the film as a wetness reducing agent, it may be desirable for aesthetic reasons to use plasticizers to produce more flexible films which resist rub-off and have reduced visibility. Examples of suitable plasticizers compatible with the polymer/solvent systems described here include phthalate esters, di- or multi-basic acid esters, and glycol derivatives. Further specific examples include diethyl phthalate, di(2-ethylhexyl phthalate), dibutyl adipate, dibutyl sebacate, acetyl triethyl citrate, butyl stearate, glyceryl triacetate, triethylene glycol di(2-ethylbutyrate).

Examples of antimicrobials suitable for use with this invention include bacteriostatic quaternary ammonium compounds such as 2-amino-2-methyl-1-propanol (AMP), cetyltrimethylammonium bromide, cetyl pyridinium chloride, 2,4,4'-trichloro-2'-hydroxydiphenylether (Triclosan), N-(4-chlorophenyl)-N'-(3,4-dichlorophenyl)urea (Triclocarban) and various zinc salts (for example, zinc ricinoleate). The bacteriostat can, illustratively, be included in the composition in an amount of 0.05–1.0%, particularly 0.1–1.0% by weight, of the total weight of the composition. Triclosan, can illustratively be included in an amount of from 0.1% to about 0.5% by weight, of the total weight of the composition.

Examples of gelling agents or thickeners suitable for use with this invention to increase the viscosity, improve aesthetics and/or improve the performance of the cosmetic compositions of the invention include one or more members selected from the group consisting of:

(a) high melting point waxes (65–101 degrees C.) such as beeswax, montan, ozokerite, ceresin, paraffin and hydrogenated castor oil;

(b) low melting point waxes (37–65 degrees C.) such as fatty alcohols, fatty acids, fatty acid esters, fatty acid amides and particularly stearyl alcohol, cetyl alcohol, stearic acid and polydimethyl siloxanyl beeswax;

(c) silicone waxes such as methyl alkyl silicone waxes and ester silicone waxes, particularly stearoxytrimethylsilane, stearyidimethicone, dimethiconol behenate and C30-45 alkyl methicone;

(d) modified natural polymers such as those which are cellulose or guar based, particularly cellulose gum, hydroxyethylcellulose, methylcellulose, hydroxypropylmethylcellulose, hydroxypropyl guar;

(e) synthetic polymers such as alkylene/alkylene oxide polymers, particularly polyethylene, oxidized polyethylene, ethylene/acrylate copolymer, ethylene/vinyl acetate copolymer, PEG-n (where n is a number from 4–90,000) and PEG-m stearate (where m is a number from 2–175);

(f) inorganic smectite clays such as smectite clays and amorphous silicon dioxide particularly hectorite, sodium magnesium silicate, stearalkonium hectorite, Quaternium-18 hectorite, bentonite, magnesium aluminum silicate, Quaternium-18 bentonite, stearalkonium bentonite, hydrated silica, and silica;

(g) trihydroxystearin and tribehenin;

(h) mixtures and blends of any of the foregoing.

For thickeners of groups a, b, and c, the addition levels are in the range of 0.05–25 percent by weight (preferably 2–17 percent) based on the total weight of the composition. For thickeners of groups d, e, f and g, the addition levels are in the range of 0.01–10% by weight (preferably 0.1–5 percent) based on the weight of the total composition.

The compositions of this invention may be made by conventional mixing techniques such as by mixing the ingredients at room temperature. The polymer is added to the solvent system with agitation. Heat may be applied if sticks are being made to melt any additional solidifying ingredients.

While the compositions of the present invention may be made initially as liquids, especially as solutions, such as, for example, 5–10 percent solutions, the compositions may, also be formulated into gels, creams or sticks (especially sticks) by techniques known to those in the art.

For liquids and sprays: 2–25% of a film former (for example, cellulose acetate butyrate); 70–95% ethyl alcohol (concentration of 95–100%); 0.05–0.3% Triclosan; and 0.5–2.5% fragrance are used. Alcohol is added to a clean, pre-weighed container. Gentle agitation (stirring) is used while adding the film former at room temperature. Stirring is continued until all the material is dissolved. The remaining ingredients which are optional (fragrance and antimicrobial) are added with stirring to obtain the complete solution.

For roll-ons: 2–25% of a film former (for example, cellulose acetate butyrate); 70–95% ethyl alcohol (95–100%); 1.0–10% PPG-10 methyl glucose ether; 0.05–0.3% Triclosan; and 0.5–2.5% fragrance are used. Alcohol is added to a clean, pre-weighed container. Gentle agitation (stirring) is used while adding the film former at room temperature. Stirring is continued until all the material is dissolved. Glucose ether is added to this solution until the desired viscosity is achieved. The remaining ingredients which are optional (fragrance and antimicrobial) are added with stirring to obtain the complete solution.

For sticks the ingredients are mixed with an appropriate molten solidifying agent at elevated temperature that is compatible with the polymer/solvent system wherein the mixture remains clear at room temperature. A particular example of a stick that may be made is as follows: 8% of a film former (for example, cellulose acetate butyrate); 79.5% ethyl alcohol (95%); 4% of propylene glycol; 4% diethyl phthalate; 2% sodium stearate; 1.5% water and 1.0% fragrance. A mixture of the film former, ethanol, propylene glycol, diethyl phthalate, sodium stearate, water and fragrance are mixed by combining the ingredients with agitation at 65 degrees C. until a clear mixture is obtained. Upon cooling, this mixture forms a clear solid product.

In the present invention the film is formed by solvent evaporation from solution. The polymer is dissolved in a solvent, such as a volatile solvent. The resulting solution can be applied to a substrate such as the skin and, as the solvent evaporates, the solution becomes more and more concentrated in polymer content, ultimately leaving behind a polymer film. The drying rate is largely regulated by changing the volatility of the solvent or solvent mixture. For the case of topical applications to humans, some solvents can also be lost from solution by absorption into the skiri. The choice of whether to use a volatile or non-volatile solvent depends on a variety of factors including the desire to create a more environmentally friendly composition with less use of volatile solvents but at the same time creating an aesthetically pleasing product that does not stay sticky for prolonged periods. The choice of solvents and polymers that will be in contact with human skin also requires that the materials not be irritating to the skin.

The cosmetic composition according to the present invention can be packaged in conventional containers, using conventional techniques. For example, where the composition is a stick composition, the composition, while still in liquid form, can be introduced into a dispensing package as conventionally done in the art, and cooled therein so as to thicken in the package. Where a gel or soft-solid cosmetic composition is produced, the composition can be introduced into a dispensing package (for example, a package having a top surface with pores) as conventionally done in the art. Thereafter, the product can be dispensed from the dispensing package as conventionally done in the art, to deposit the active material, for example, on the skin. This provides good deposition of the active material on the skin.

The composition may be applied to the skin (especially underarm mammalian skin) using conventional techniques and applicators and in a manner that would result in typical loading as used for underarm products. For example, for use as an antiperspirant and/or deodorant is preferably in the range of 0.5–10 mg/cm$^2$, for example, in the range of 2–6 mg/cm$^2$ and especially 4 mg/cm$^2$. For example, the system may be applied at a volume dosage of about 4 microliters/cm$^2$. If a solution having a 10 percent polymer content is used, this will produce a film of about 4 microns in thickness.

In order to provide the desirable properties, the film formed by application of the composition to the skin should have a pencil hardness greater than or equal to 6B and a water uptake of less than 5 weight percent when exposed to conditions of 75 percent relative humidity at 25 degrees C.

A desired feature of the present invention is that some embodiments provide a clear, or transparent, cosmetic composition, (for example, a clear or transparent deodorant or antiperspirant composition). The term clear or transparent according to the present invention is intended to connote its usual dictionary definition; thus, a clear, for example, stick or gel antiperspirant composition of the present invention allows ready viewing of objects behind it. By contrast, a translucent composition, although allowing light to pass through, causes the light to be scattered so that it will be impossible to see clearly objects behind the translucent composition. An opaque composition does not allow light to pass therethrough. Within the context of the present invention, a gel or stick is deemed to be transparent or clear if the maximum transmittance of light of any wavelength in the range 400–800 nm through a sample 1 cm thick is at least 35%, preferably at least 50%. The gel or stick is deemed translucent if the maximum transmittance of such light through the sample is between 2% and less than 35%. A gel or stick is deemed opaque if the maximum transmittance of light is less than 2%. The transmittance can be measured by placing a sample of the aforementioned thickness into a light beam of a spectrophotometer whose working range includes the visible spectrum, such as a Bausch & Lomb Spectronic 88 Spectro-photometer. As to this definition of clear, see European Patent Application Publication No. 291,334 A2. Thus, according to the present invention, there are differences between transparent (clear), translucent and opaque compositions.

In one particular alcohol/soap/water embodiment which may be used to form a clear stick, an alcohol system consisting of predominantly ethanol is used with a small amount of propylene glycol to prevent excessively rapid drying. Sodium stearate is used as the solidifying agent and the ingredients are mixed with agitation at about 65 degrees C. until clear. The general amounts that may be used are 60–85 percent ethanol (SD40, 190 proof (95%)); 0.5–20 percent polymer (for example 5–10 percent); 1–8 percent of sodium stearate (OP 200M from RTD Chemical Corp., Hackettstown, N.J.), 1–8 percent water; and 4–12 percent propylene glycol. Optionally, up to 4 %, preferably 2% fragrance may be included.

The polymer stick formulations (such as those made with 10 percent polymer) may be made with considerably lower levels of sodium stearate (about 2–4 percent) than used in conventional deodorant sticks. In one example of such a formulation, 10 percent of CAB 553-0.4 is combined with 2 percent sodium stearate and 12 percent propylene glycol. While the presence of a polymer film may be detected after application to the forearm of a human test subject, it is less visible than when delivered from a straight ethanol solution; this indicates a benefit from the inclusion of propylene glycol.

In a preferred embodiment a clear stick is formed and is applied at a dosage rate of approximately 4 mg/cm$^2$.

In another embodiment with CAP 504-0.2 as the polymer, it was found that when using this type of polymer the incorporation of diethylphthalate as a plasticizer (for example, at a polymer:plasticizer ratio of 2:1) virtually eliminated any white residue. In one particular formulation, 79.5 percent ethanol (SD40 190 proof (95 percent)); 8.0 percent-CAP 504-0.2; 4.0 percent propylene glycol; 4.0 percent diethyl phthalate; 2.0 percent sodium stearate (OP200); 1.5 percent water; 1.0 percent fragrance can be combined with or without a coloring agent. The percents are weight percents based on the total weight of the composition.

In evaluating the performance of the compositions of this invention several parameters were found to be important. These were film hardness, solution viscosity and water solubility in the film. Also, reduction in wetness as determined by a forearm sweat test was performed.

FILM HARDNESS—Films for determining hardness were prepared from 10 percent weight/volume solutions in ethanol or ethanol containing up to 10 percent water. The solutions can be applied to glass plates (such as a glass microscope slide) by means of a cotton applicator (such as a swab) or by dipping. The solvent may be allowed to evaporate for a period of 24 hours, although a three hour drying time for ethanol solutions can be sufficient to allow evaporation of solvent and achieve consistent results. Hardness was evaluated by the pencil hardness method, which is described in ASTM D3363, and incorporated by reference in its entirety herein. In particular, the "gouge hardness" was measured. Pencil leads with lead holder were obtained from an office supply warehouse store (2 mm diameter) with hardness grades as noted in Table I ordered from softest to hardest.

TABLE I

| 6B | 5B | 4B | 3B | 2B | B | HB | F | H | 2H | 3H | 4H | 5H | 6H | 7H | 8H | 9H |
|----|----|----|----|----|---|----|---|---|----|----|----|----|----|----|----|----|
| SOFT ────────────────────────────────────────────────→ HARD |

To conduct the test each lead was ground on abrasive paper to expose a flat (no point) 2 mm diameter surface normal to the lead axis. The pencil was held at a 45 degree angle to the film surface and pushed into and along the surface with enough force to either cut the film or crush the lead. The lead was reground before each test or rotated so that a fresh edge was in contact with the film. Three passes were made for each lead. The film hardness is reported as that of the hardest lead which does not cut the film. Repeat tests indicate that the uncertainty in this method is one pencil hardness increment.

SOLUTION VISCOSITIES—Solution viscosities of 10 weight percent solutions in ethanol or ethanol containing up to 10 weight percent water can be obtained using a Brookfield viscometer.

WATER UPTAKE—Water uptake of polymers was evaluated by placing previously degassed films or powders in a 75 percent relative humidity environment at 25 degrees C. The water uptake at equilibrium was determined gravimetrically using standard procedures.

FOREARM SWEAT REDUCTION TEST—Reduction of wetness was evaluated by a forearm sweat reduction test as described below. An indicator method was established which uses the color change associated with the reaction of elemental iodine and starch to form a blue-black complex as is known in the art. The method uses a test patch which consists of a paper strip (starch source) that has been impregnated with iodine. The paper used was office letterhead bond paper (25 percent cotton). The iodine treatment was conducted by dipping the office paper in a one percent solution in ethanol. The paper was immediately placed in a dry environment (less than 20 percent relative humidity), preferably in a desiccator, for 1–3 hours. Failure to keep the paper dry immediately after exposure to the iodine solution resulted in premature reaction, causing the entire paper to become discolored and unacceptable for further use. After several hours in the dry environment, the paper could be placed in ambient conditions. In fact, it is recommended that the paper be aired out in this fashion for at least one hour prior to use, to eliminate residual iodine odor and background tint. This treated paper will give a purple/brown color indication at points where it comes into contact with water. The paper's ability to detect and quantify sweat output was determined in preliminary testing, in which test strips were taped with Highland transparent tape to the inside of the forearms of seven people. A strip size of 1.5×0.5 inches (38 mm×13 mm) was used. Subjects then sat in a room maintained at a temperature in the range of 98–104 degrees F. (37 to 40degrees C.). Test strips were removed periodically over a 10 minute period. For five of the subjects the strips clearly showed developing sweat patterns appearing as dark spots on the patch which became more intense with time. Two subjects did not sweat appreciably after the full 10 minute interval.

Tests were also conducted which indicated that this forearm test could distinguish sweat output between regions treated with standard antiperspirant and regions left untreated. An antiperspirant material (30 percent solution of aluminum chlorohydrate (Reach 101 Micro Aluminum Chlorohydrate (ACH)) in deionized water from Reheis) was prepared and used within one hour of preparation. The solution was applied to forearms of five subjects at a level of 50 microliters inside of a predrawn rectangle measuring 7.5×3.0 cm. After application with a pipette, the solution was spread by finger to evenly cover the entire test area and then the coating was allowed to dry. The application was repeated on the morning of three consecutive days. On the afternoon of the third day, multiple test patch strips were applied to the subjects' forearms such that half of each strip was placed over the treated region inside the rectangle while the other half was left over untreated skin. Strips were removed after hot room testing as described above. Because different regions on the arm may produce different sweat outputs and because strips were removed at different times in attempts to achieve optimum levels of sweat exposure for good patterns, each strip is considered an isolated test containing an individual comparison between an adjacent treated and untreated area. For all of the subjects tested, clear reductions in sweat output were observed in areas treated with the antiperspirant.

For compositions of the invention a similar protocol was followed. A 7.5×3.0 cm rectangle was drawn on the forearm of each subject as the test area. A polymer solution was applied at a 90 microliter level and spread to cover the entire area. This corresponds to a dosage level of 4.0 microliters/$cm^2$, which is comparable to levels employed in standard underarm testing. For a 10 percent polymer solution this also corresponds to an expected polymer film thickness on the skin of approximately 4 micrometers. Typically one test was conducted per arm. In a standard test the solvent was allowed to evaporate and the remaining film was left on the forearm with shirtsleeve down for a period of 1–1.5 hours. After this time the test patches were applied, two for each rectangle made with the test polymer, again with half of each patch inside the rectangle and half outside the rectangle. Sweating was then initiated in the hot room as described above. Some experience was required to use an exposure time sufficient to result in appropriate sweat patterns but not to the point where individual droplets ran into each other so that the patch became saturated. In general, patches were removed at a point where a droplet pattern became visibly distinguishable through the paper.

Evaluation of the patches obtained from the forearm test can be performed by image analysis of sweat patterns appearing on the patches. An appropriate measure is the fraction of the test patch area that is covered with spots from sweat droplets. This can be done visually by total sweat visualization of the area and/or by computer analysis. For purposes of comparison, compounds will be considered effective when a decrease in area of perspiration greater than 15%, more particularly 20%, and especially 25% is achieved. As explained above, FIG. 1 shows a representative sample of the extent over which the droplet pattern covered the sample section of the forearm observed in treated areas as compared to untreated areas. As noted for FIG. 1, a rating of 0 has a dot pattern with about the same appearance as the control; a rating of 1 has fewer dots; and a rating of 2 has very few dots.

It should also be noted that-the compositions of the present invention can also be used on other parts of the body such as the face where it is desirable for cosmetic reasons to reduce wetness. Since the compositions of the present invention do not require the presence of an antiperspirant to achieve the desired effect, there is less concern about putting such compositions on the face because of the reluctance to apply antiperspirant actives to that area, such as for persons in front of hot lights for television or theatrical productions.

As described herein where the term comprising is used it is also meant to include consisting of and consisting essentially of.

EXAMPLES

The following Examples are offered as being illustrative of the invention but should not be construed as limitations thereon. In the Examples and elsewhere in this application, chemical terms have their usual and customary meanings and all percents are in weight percents based on the weight of the total composition unless indicated otherwise. For the following Examples the following materials were used:

cellulose acetate propionate—hydroxyl content of approximately 5.0 weight percent (CAP 504-0.2 from Eastman Chemical Company, Kingsport, Tenn.).

cellulose acetate butyrate—with high hydroxyl content (CAB 553-0.4 from Eastman Chemicals, Kingsport, Tenn.).

Examples 1–3

Pencil hardness values were determined for Example 1: cellulose acetate butyrate (CAB 553-0.4); Example 2: cellulose acetate propionate (CAP 504-0.2); and Example 3: cellulose acetate butyrate containing diethyl phthalate as a plasticizer. Samples were cast from solutions in ethanol (Examples 1 and 3) or 90% ethanol/10% water (Example 2) onto glass, and pencil hardness tests were conducted as described above. Solutions for Examples 1 and 2 contained 10% polymer. The Example 3 solution contained 10% polymer and 5% diethyl phthalate. The pencil hardness for each of Examples 1 and 2 was F. The pencil hardness for Example 3 was 2B.

Examples 4–7

Solutions of the polymers as listed in Table 11 were made by combining the ingredients with agitation at room temperature. Additionally, a salt solution and propylene glycol were made or obtained. Forearm sweat reduction tests were done for the compositions listed in Table II using the procedure described above. After application of solutions to the forearm, each polymer solution left behind a fairly smooth polymer film whose presence could be detected visually with proper lighting, by touch, or by deformation of the skin to reveal some difference in flexibility between the coated and uncoated regions. It is noted that the 10 percent level of polymer in most of the solutions is at the upper range of the recommended 5–10% range. The Efficacy Scale of FIG. 1 was used.

TABLE II

| Composition | Effective in Forearm Sweat Reduction Test | Efficacy Rank (Scale of FIG. 1) | Pencil Hardness (Scale of Table 1) | Equilibrium $H_2O$ Uptake in % at 25 degrees C. and 75% relative humidity |
|---|---|---|---|---|
| Example 4: CAB 553-0.4 (10% in absolute ethanol) | Yes | 2 | F | 3 |
| Example 5: CAP 504-0.2 (10% in 90/10 ethanol/water) | Yes | 1 | F | 4.5 |
| Example 6: Poly(dimethylsiloxane) gum (SE30), General Electric) (10% in hexamethyldisiloxane) | No | 0 | <6B | <1 |
| Example 7: Vinyl acetate vinyl pyrrolidone copolymer (LUVISKOL VA 37, BASF) (10% in absolute ethanol) | No | 0 | H | 8 |
| Propylene glycol | No | 0 | na | na |
| NaCl Solution | No | 0 | na | na |

TABLE II-continued

| Composition | Effective in Forearm Sweat Reduction Test | Efficacy Rank (Scale of FIG. 1) | Pencil Hardness (Scale of Table 1) | Equilibrium $H_2O$ Uptake in % at 25 degrees C. and 75% relative humidity |
|---|---|---|---|---|
| (10% in water) | | | | |

Example 8

The Forearm Sweat Reduction Test described for Example 4 was repeated with the cellulose acetate butyrate except that the hot room test was conducted for 6 hours after application. The polymer remained effective as evaluated by the sweat test and received an Efficacy Rank of 2.

Example 9

The method of Example 5 may be repeated with 95% (190 proof) alcohol.

Example 10

A mixture of 10 wt % cellulose acetate butyrate (CAB 553-0.4), 87.5 wt % ethanol (100%, 200 proof) and 2.5 wt % diethyl phthalate (as a plasticizer) was made by combining the ingredients with agitation at room temperature. The resulting liquid was tested for sweat reduction using the Forearm Sweat Reduction Test described above. The test results indicated a significant reduction in sweat over the observed area and had an Efficacy Rank of 2.

Example 11

A mixture of 10 wt % cellulose acetate butyrate (CAB 553-0.4), 8.5 wt % ethanol (100%, 200 proof) and 5 wt % diethyl phthalate (as a plasticizer) was made by combining the ingredients with agitation at room temperature. The resulting liquid was tested for sweat reduction using the Forearm Sweat Reduction Test described above. The test results indicated a significant reduction in sweat over the observed area and had an Efficacy Rank of 2.

Example 12

A mixture of 10 wt % cellulose acetate butyrate (CAB 553-0.4), 2 wt % sodium stearate, 12 wt % propylene glycol, and 76 wt % ethanol (95%, 190 proof) was made by combining the ingredients with agitation at 65 degrees C. until clear. Upon cooling, this mixture formed a clear solid product. The resulting liquid was tested for sweat reduction at a dosage rate of 4 mg/cm$^2$ using the Forearm Sweat Reduction Test described above. The test results indicated a significant reduction in sweat over the observed area and had an Efficacy Rank of 2.

Example 13

The method of Example 12 was repeated except that the product was applied at a dosage rate of 2 mg/cm$^2$. The resulting liquid was tested for sweat reduction using the Forearm Sweat Reduction Test described above. The test results indicated a significant reduction in sweat over the observed area and had an Efficacy Rank of 1.

Example 14

The method of Example 12 was repeated except that the forearm test was conducted 6 hours after application instead of the normal protocol of 1–1.5 hours. The resulting liquid was tested for sweat reduction using the Forearm Sweat Reduction Test described above. The test results indicated a significant reduction in sweat over the observed area and had an Efficacy Rank of 2.

Example 15

A mixture of 8 wt % cellulose acetate propionate (CAB 504-0.2), 79.5 wt % ethanol (95%, 190 proof), 4 wt % propylene glycol, 4 wt % diethyl phthalate, 2 wt % sodium stearate, 1.5 wt % water and 1 wt % fragrance was made by combining the ingredients with agitation at 65 degrees C. until clear. Upon cooling, this mixture formed a clear solid product. The resulting liquid was tested for sweat reduction at a dosage rate of 4 mg/cm$^2$ using the Forearm Sweat Reduction Test described above. The test results indicated a significant reduction in sweat over the observed area and had an Efficacy Rank of 2.

What is claimed is:

1. An underarm product selected from the group consisting of an antiperspirant, a deodorant and a combination antiperspirant/deodorant which reduces or eliminates wetness caused by perspiration, wherein the underarm product comprises a film forming system comprising an ester component which is a cellulose ester or mixture of cellulose esters, and is capable of forming a thin film on the skin, which film is characterized by a pencil hardness greater than or equal to 6B; and wherein the film forming system comprises:

(a) an alcohol-based solvent system selected from the group consisting of
      (i) a volatile aliphatic alcohol containing up to 10 weight percent water and having a solubility parameter in the range of 20.5–31.0 (MPa)$^{1/2}$, wherein the alcohol is selected from the group consisting of ethanol, n-propanol, isopropanol, n-butanol, isobutanol, and mixtures of any of the foregoing; and
      (ii) a solvent as described in part (i) in combination with a nonvolatile polyhydric glycol selected from the group consisting of propylene glycol, dipropylene glycol, tripropylene glycol, other polypropylene glycols, and glycerol, provided that the ratio of propylene glycol, dipropylene glycol, tripropylene glycol, other polypropylene glycols, and glycerol to aliphatic alcohol does not exceed 1:5; and (b) a cellulose ester or a mixture of cellulose esters which is:
      (i) soluble in the alcohol-based solvent system wherein the cellulose ester is added in an amount between 0.5–20 weight percent based on the total composition; and
      (ii) has an ester group formed with 2–6 carbons and an average hydroxyl content of at least 3.00%.

2. The underarm product of claim 1 wherein the cellulose ester component is soluble in an alcohol-based solvent system in an amount between 0.5–10 weight percent based on the total composition.

3. The underarm product of claim 1 wherein, after application to the skin, the product forms a film having (a) a thickness in the range of 0.1–10 microns; (b) a pencil hardness greater than or equal to 6B; and (c) a water absorbing capability at equilibrium of less than 5 weight percent water when exposed to a condition of 75 percent relative humidity at 25 degrees C.

4. The underarm product of claim 1 wherein the film forming system is made as a 5–10% solution with a viscosity of less than 5,000 centipoise.

5. The underarm product of claim 4 wherein the film forming system is made as a 5–10% solution with a viscosity of less than 1,000 centipoise.

6. The underarm product of claim 5 wherein the film forming system is made as a 5–10% solution with a viscosity of less than 350 centipoise.

7. The underarm product of claim 1 additionally comprising at least one member selected from the group consisting of emollients, surfactants, small particulates, plasticizers, fragrances, antiperspirant salts, antimicrobials, and solidifying agents.

8. The underarm product of claim 7 comprising an antiperspirant salt in an amount of 0.1–30% by weight based on the total weight of the composition.

9. The underarm product of claim 8 comprising an antiperspirant salt in an amount of 5–25% by weight based on the total weight of the composition.

10. The underarm product of claim 8 comprising an antiperspirant salt in an amount of 0.1–5% by weight based on the total weight of the composition.

* * * * *